(12) United States Patent
Neven

(10) Patent No.: US 10,336,677 B2
(45) Date of Patent: Jul. 2, 2019

(54) CURCUMIN PURIFICATION

(71) Applicant: BIOPTEQ SPRL, Nandrin (BE)

(72) Inventor: Philippe Neven, Nandrin (BE)

(73) Assignee: BIOPTEQ SPRL, Nandrin (BE)

( * ) Notice: Subject to any disclaimer, the term of this patent is extended or adjusted under 35 U.S.C. 154(b) by 0 days.

(21) Appl. No.: 16/087,895

(22) PCT Filed: Mar. 16, 2017

(86) PCT No.: PCT/EP2017/056240
§ 371 (c)(1),
(2) Date: Sep. 24, 2018

(87) PCT Pub. No.: WO2017/162511
PCT Pub. Date: Sep. 28, 2017

(65) Prior Publication Data
US 2019/0039983 A1     Feb. 7, 2019

(30) Foreign Application Priority Data
Mar. 25, 2016   (EP) .................................... 16162467

(51) Int. Cl.
*C07C 45/85*   (2006.01)

(52) U.S. Cl.
CPC .................... *C07C 45/85* (2013.01)

(58) Field of Classification Search
CPC .................................................... C07C 45/85
See application file for complete search history.

(56) References Cited

FOREIGN PATENT DOCUMENTS

| CN | 1534013 A | 10/2004 |
|---|---|---|
| WO | WO-06129323 A1 | 12/2006 |
| WO | WO-09144220 A1 | 12/2009 |

OTHER PUBLICATIONS

Abcam Biochemicals: "Curcumin (high purity) (ab141921)", Retrieved from the Internet <URL:http://www.abcam.com/curcumin-high-purity-ab141921.html>, access date Sep. 21, 2018 (2 pages).
Database Chemcats [online] Chemical Abstract Services, Colombus, Ohio, US; Jul. 16, 2014 (Jul. 16, 2014), Abcam Biochemicals Product List: "Curcumin in high purity", XP002759916, Database accession No. 0164164065, Jul. 16, 2014 (1 page).
P. Basnet et al.: "curcumin: an anti-inflammatory molecule from a curry spice on the path to cancer treatment", Molecules, vol. 16, Jun. 3, 2011 (Jun. 3, 2011), pp. 4567-4598, XP002769801.

*Primary Examiner* — Sikarl A Witherspoon
(74) *Attorney, Agent, or Firm* — Harness, Dickey & Pierce, P.L.C.

(57) ABSTRACT

The present invention relates to a process for the purification of curcumin comprising provision of a curcuminoid composition, contacting said curcuminoid composition with basic amino acid or amino acid ester in order to form an amino acid salt of curcumin, separating the salt of curcumin, and recovering curcumin at increased purity levels. Curcumin may be obtained at purity levels beyond 90 wt. %.

14 Claims, No Drawings

CURCUMIN PURIFICATION

CROSS-REFERENCE TO RELATED APPLICATIONS

This application is a U.S. National Stage of International Application No. PCT/EP2017/056240, filed on Mar. 16, 2017, which claims the benefit of, and priority to, European Patent Application No. 16162467.1, filed on Mar. 25, 2016. The entire disclosures of the above applications are incorporated herein by reference.

The present invention relates to a process for the purification of curcumin, more specifically a purification process starting from a curcuminoid composition.

Curcumin is a major curcuminoid derived from the curry spice turmeric. It's chemical structure is shown below in its enol form and ketone form.

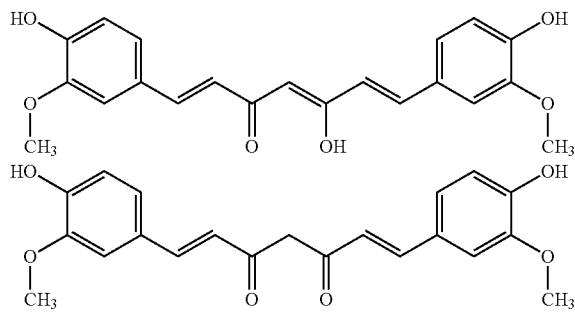

Curcumin is known for its anti-oxidant, anti-amyloid and anti-inflammatory properties. Further, anti-cancer activity has been documented in recent years. In the light of this, curcumin is an important pharmaceutically active ingredient.

While curcumin shows significant biological activity, its physico-chemical properties do not appear to encourage further clinical development because of its inappropriate absorption, distribution and excretion in vivo. Combinations of curcumin with piperidine appears to increase bioavailability of curcumin. Also complexing curcumin with phospholipids may increase its incorporation into lipophilic membranes. Emulsions of curcumin have also shown increased bioavailability in rodents. WO2009/144220 discloses cyclodextrin complexes of curcumin or arginine or lysine salts of curcumin, which appear to show improved solubility in water and improved biological activity when administered per os.

In the light of the known pharmacological activity of curcumin and of the ongoing efforts to improve curcumin bioavailability in vivo through different approaches including development of new galenic forms or delivery systems, there is a perceived need for pure curcumin. Synthetic routes to curcumin production are known which are, however, tarnished by the drawbacks of such chemical synthesis. On the other hand, known curcumin extraction processes provide (standard) curcuminoid compositions that contain at best 75 to 80 wt. % pure curcumin, in combination with other curcuminoids, such as demethoxycurcumin and bis-demethoxycurcumin, and impurities, such as phenols and other impurities. Purification to curcumin levels beyond 90 wt. % would hence be desirable.

The term "curcuminoid" as used herein is understood to mean curcumin in its enol and ketone form, demethoxycurcumin and bisdemethoxycurcumin. The term "curcumin" has been defined here above.

The present invention thus seeks to provide a process, more specifically an industrial process, for the enrichment or purification of curcumin to high levels of purity, preferably higher than 90 wt % pure curcumin.

It has now been found that curcumin may be obtained at high levels of purity, such as more than 90 wt. %, by contacting a curcuminoid composition with a basic amino acid, e.g. lysine, arginine or histidine, or derivatives of amino acids, such as esters or amides of amino acids, or mixtures thereof, in order to form an amino acid salt of curcumin, separating the salt, and recovering curcumin at increased purity levels.

Lysine, arginine and histidine are amino acids known for their relatively high basic character due to the primary amino group at a distant end from the carboxyl group. Amino acid esters also are suitable as far as they show suitable basic character. Other derivatives of amino acids that show the required basic character are also suitable. Curcumin, on the other hand, shows acidic character around the enol part of the molecule. The formation of amino acid salts, more particularly lysine and/or arginine salts of curcumin may be effected in an appropriate solvent.

The solvent may be a polar alcoholic solvent in which curcumin and the basic amino acid or ester of amino acid and curcumin salt are soluble, for example methanol. Other examples of appropriate solvent are acetone, ethyl methyl ketone, ketone and ethyl acetate.

The formed salt or salts may be allowed to precipitate, for instance by concentrating the solution containing said salt or salts and/or by adding a solvent in which the formed salt is not soluble, and the separation of the salt or salts may then be carried out by filtration or equivalent means. The recovered salt or salts may be further dried, for example to a level of less than 2% w/w, if so desired, for intermediate storage or further processing.

The recovered salt may then be redissolved in water for instance and the solution be acidified in order to recover solid curcumin for instance by filtration. The solid curcumin may be further washed and/or dried according to known methods.

It is to be understood and it is known to the skilled person that the above process steps, including amino acid salt formation step and acidification step, may be repeated in order to further increase the purity level of the curcumin obtained. It has been found that curcumin may hence be recovered at a purity level significantly beyond 90 wt. %.

The invention process may advantageously be performed on a standard curcuminoid extract. Such extracts are readily available and generally prepared at proximity of the growing of the relevant turmeric plant. These comprise curcumin, in enol and ketone form, and the curcuminoids, demethoxycurcumin and bisdemethoxycurcumin. While the curcuminoid concentration of these extracts may be rather high (as high as 95 wt. % or even more), the curcumin concentration generally varies between 55 and 85 wt. %.

The invention process has shown to be a simple, industrially applicable process that is capable of enriching a curcuminoid composition in curcumin up to levels higher than 90 wt. % curcumin. As can be seen from the description above, the process is operable with high yields. Since the process clearly is not a synthetic route to produce curcumin, the obtained curcumin may be used in applications, such as neutraceuticals and food additives, at reduced registration costs.

The invention will be described in more details herein below with reference to an Example.

EXAMPLE

An aliquot of 3.5 g of standardized curcuminoid extract (CAS N° 458-37-7) containing 75-80 wt. % curcumin in its enol and ketone form, together with demethoxycurcumine and bisdemethoxycurcumine and other impurities (Sigma Aldrich) is solubilized in 400 ml methanol under stirring and heated at 35° C. during 5 minutes. A yellow solution is obtained. The insoluble residue (a brownish resin) is filtered and eliminated.

A fraction of 1.388 g of lysine base is added to the filtrate under agitation. The solution becomes bordeaux red. After 5 additional minutes of stirring, the solution is concentrated under vacuum at 25° C. such as to reduce its volume to approx. 50 ml. 250 ml of ethanol are added under stirring. The obtained curcumin lysinate salt is recovered by filtration and dried. Approx 4 g of salt are obtained.

A 2 g aliquot of the curcumin lysinate salt obtained above are dissolved in 200 ml of water at 25° C., under stirring. The solution is acidified to pH=1 by addition of concentrated hydrochloric acid. A yellow curcumine precipitate settles and is recovered by filtration and washed with water. The purity is higher than 95%. Yield has been computed to be higher than 90%.

In order to further increase purity level of curcumin, the steps described above may be repeated. The product obtained may be used to form a salt with lysine base again; the salt may be recovered as described above and redissolved it in water, followed by addition of hydrochloric acid.

What is claimed is:

1. A process for purification of curcumin comprising:
   (i) providing a curcuminoid composition;
   (ii) contacting said curcuminoid composition with a basic amino acid or an amino acid derivative to form an amino acid salt of curcumin;
   (iii) separating the salt of curcumin; and
   (iv) recovering purified curcumin.

2. The process of claim 1, wherein the basic amino acid is selected from the group consisting of lysine, arginine and histidine.

3. The process of claim 1, wherein the amino acid salt of curcumin is formed in a polar alcoholic solvent in which the curcumin, the basic amino acid, or the amino acid derivative and the amino acid salt of curcumin are soluble.

4. The process of claim 1, wherein separating the curcumin salt occurs by concentrating the solution containing said salt, thereby precipitating the salt.

5. The process of claim 1, wherein separating the curcumin salt includes adding a solvent in which the curcumin salt is not soluble.

6. The process of claim 4, wherein the precipitate is filtered.

7. The process of claim 1, further comprising drying the recovered curcumin salt.

8. The process of claim 1, wherein recovering purified curcumin further comprises redissolving the salt in solution and acidifying the solution.

9. The process of claim 8, wherein said salt is redissolved in water.

10. The process of claim 8, wherein curcumin is recovered by filtration, washed and possibly dried.

11. The process of claim 1, wherein steps (ii), (iii) and (iv) are repeated.

12. The process of claim 1, wherein the amino acid derivative is an ester or carboxamide.

13. The process of claim 2, wherein the basic amino acid is lysine or arginine.

14. The process of claim 13, wherein the basic amino acid is lysine.

* * * * *